United States Patent

Scholz et al.

[11] Patent Number: 5,286,406
[45] Date of Patent: Feb. 15, 1994

[54] LIQUID BODY-CLEANSING AGENTS BASED ON ALKYL GLYCOSIDES

[75] Inventors: Wolfhard Scholz; Gryta Schosser; Werner Schneider; Heike Schelges, all of Krefeld; Marianne Waldmann-Laue, Langenfeld, all of Fed. Rep. of Germany

[73] Assignee: Henkel Kommanditgesellschaft auf Aktien, Duesseldorf, Fed. Rep. of Germany

[21] Appl. No.: 927,479

[22] PCT Filed: Mar. 18, 1991

[86] PCT No.: PCT/EP91/00516

§ 371 Date: Sep. 28, 1992

§ 102(e) Date: Sep. 28, 1992

[87] PCT Pub. No.: WO91/14761

PCT Pub. Date: Oct. 3, 1991

[30] Foreign Application Priority Data

Mar. 26, 1990 [DE] Fed. Rep. of Germany ....... 4009616

[51] Int. Cl.$^5$ .................. C11D 3/22; C11D 3/04; C11D 3/32
[52] U.S. Cl. .................. 252/174.17; 252/173; 252/546; 252/DIG. 5; 252/DIG. 13; 252/DIG. 14
[58] Field of Search ............ 252/174.17, 546, DIG. 5, 252/DIG. 13

[56] References Cited

U.S. PATENT DOCUMENTS

| | | | |
|---|---|---|---|
| 3,547,828 | 12/1970 | Mansfield et al. | 252/351 |
| 3,707,535 | 12/1972 | Lew | 260/210 |
| 3,772,269 | 11/1972 | Lew | 260/210 |
| 3,839,318 | 10/1974 | Mansfield | 260/210 |
| 3,898,129 | 8/1975 | Fujimoto et al. | 195/29 |
| 4,349,669 | 9/1982 | Klahr et al. | 536/127 |
| 4,411,884 | 10/1983 | Jacquet et al. | 424/47 |
| 4,517,174 | 5/1985 | Jacquet et al. | 424/62 |
| 4,543,205 | 9/1985 | Contamin | 252/546 |
| 4,668,422 | 5/1987 | Malik et al. | 252/174 |
| 4,673,525 | 6/1987 | Small et al. | 252/132 |
| 4,702,906 | 10/1987 | Jacquet et al. | 424/70 |
| 4,732,696 | 3/1988 | Urfer | 252/174.17 |
| 4,814,166 | 3/1989 | Vanlerberghe et al. | 424/70 |
| 4,919,846 | 4/1990 | Nakama et al. | 252/542 |
| 4,960,541 | 10/1990 | Kanekiyo | 252/546 |
| 5,073,293 | 12/1991 | Deguchi et al. | 252/174.17 |
| 5,076,953 | 12/1991 | Jordan et al. | 252/108 |

FOREIGN PATENT DOCUMENTS

| | | |
|---|---|---|
| 0077167 | 4/1983 | European Pat. Off. . |
| 0133345 | 2/1985 | European Pat. Off. . |
| 0203750 | 12/1986 | European Pat. Off. . |
| 0339498 | 11/1989 | European Pat. Off. . |
| 0356784 | 3/1990 | European Pat. Off. . |
| 1943689 | 8/1969 | Fed. Rep. of Germany . |
| 2036472 | 7/1970 | Fed. Rep. of Germany . |
| 2252281 | 10/1972 | Fed. Rep. of Germany . |
| 3001064 | 1/1980 | Fed. Rep. of Germany . |
| 936632 | 7/1948 | France . |
| 63-30599 | 2/1988 | Japan . |
| 1-178597 | 7/1989 | Japan . |
| 745367 | 2/1956 | United Kingdom . |

*Primary Examiner*—Paul Lieberman
*Assistant Examiner*—A. Hertzog
*Attorney, Agent, or Firm*—Ernest G. Szoke; Wayne C. Jaeschke; Norvell E. Wisdom, Jr.

[57] ABSTRACT

Aqueous detergent preparations containing 1–20 wt. % of a condensation product of fatty acids with 12–22 carbon atoms and water-soluble oligo- and/or polypeptides and their water-soluble salts, and 1–20 wt. % of an alkyl glycoside are characterized by their excellent foaming capacity and increased viscosity or ease of thickening on addition of 1–8 wt. % of an amphoteric or zwitterionic tenside and/or 0.1–5 wt. % of a water-soluble, inorganic electrolytic salt, e.g. a chloride or sulphate of an alkali metal or magnesium.

20 Claims, No Drawings

LIQUID BODY-CLEANSING AGENTS BASED ON ALKYL GLYCOSIDES

FIELD OF THE INVENTION

This invention relates to water-based detergent preparations which are particularly suitable for use as liquid or paste-form personal hygiene preparations and which show increased viscosity, good thickenability by addition of water soluble electrolyte sales and improved foaming power and which contain a combination of protein hydrolyzate/fatty acid condensation products (PFC) and alkyl glycosides.

STATEMENT OF RELATED ART AND OBJECT OF THE INVENTION

Protein/fatty acid condensates are a well-known class of surfactants which, by virtue of their compatibility with the skin, are recommended for cosmetic cleaning preparations. However, they show poor foaming power and, in the form of aqueous solutions, cannot be effectively thickened by addition of electrolytes. Accordingly, they have to be combined with high-foaming, readily thickenable anionic surfactants so that their high compatibility with the skin is impaired. Accordingly, there was a need to find a suitable surfactant partner for surfactants of the protein/fatty acid condensate type which would enable the foaming properties to be improved and their viscosity to be readily increased without any reduction in compatibility. These properties are particularly important for cosmetic personal hygiene preparations such as, for example, liquid soaps, shower baths, bath preparations, cosmetic washing pastes, hair rinses and hair shampoos, because these products are distibuted by hand over the head or body and, accordingly, require a certain viscosity to prevent them from running through the fingers like water. However, such properties are also desirable in liquid light-duty detergents and dishwashing detergents.

DESCRIPTION OF THE INVENTION

It has now been found that, by combining protein/-fatty acid condensates with alkyl glycosides, it is possible to produce particularly interesting water-based detergent preparations which not only combine the advantages of both classes of surfactant, they also shown new unexpected properties.

SUMMARY OF THE INVENTION

Accordingly, the present invention relates to water-based detergent preparations containing
 (A) 1 to 20% by weight of a condensation product of fatty acids containing 12 to 22 carbon atoms and, water-soluble oligo- and/or poly-peptides, preferably protein hydrolyzates or a water-soluble salt thereof and
 (B) 1 to 20% by weight of an alkyl glycoside corresponding to the formula $R^1$-$(G)_x$, in which $R^1$ is an alkyl group containing 8 to 22 carbon atoms and $(G)_x$ is a glucoside or oligoglycoside unit having a degree of oligomerization x of 1 to 10. The detergent preparations according to the invention have a higher viscosity—or, for lower surfactant concentrations, better thickenability by addition of electrolytes—than preparations containing only one of the two components. In addition, the foaming power of the preparations according to the invention is synergistically increased. Condensation products of fatty acids and oligopeptides or polypeptides are, above all, the known condensation products of fatty acids and protein hydrolyzates. To this end, proteins, for example soya protein, collagen or keratin are first subjected to hydrolysis to form water soluble oligopeptides and/or polypeptides. The oligopeptides and/or polypeptides are then acylated with fatty acid chlorides. However, it is also possible, for example in accordance with FR-PS 936 632, to heat the alkali metal salt of the peptide with the fatty acid soap to temperatures of 130° C. to 220° C. The salts of the protein hydrolyzate/fatty acid condensates obtainable in this way are commercially available in the form of aqueous solutions under the names of Lamepon ® or Maypon ®.

Alkyl glycosides corresponding to the formula $R^1$-$(G)_x$ are well-known surface-active agents which may be produced from sugars and aliphatic, primary alcohols containing 8 to 22 carbon atoms by acetalization. Preferred sugar components (glycoses) are glucose and also fructose, mannose, galactose, talose, gulose, allose, altrose, idose, arabinose, xylose, lyxose, ribose and mixtures thereof. By virtue of their ready availability and their favorable performance properties, it is preferred to use the acetalization products of glucose with fatty alcohols ($R^1$—OH) which may be obtained, for example, from natural oils and fats by known methods, more particularly using linear, primary, saturated and unsaturated fatty alcohols containing 8 to 22 carbon atoms.

Alkyl glycosides corresponding to the formula $R^1$-$(G)_x$, their production and their use as surface-active agents are known, for example, from US-A-3,839,318, US-A-3,707,535, US-A-3,547,828, DE-A-19 43 689, DE-A-20 36 472, DE-A-30 01 064 and EP-A-77 167.

So far as the glycoside unit $-(G)_x$ is concerned, both monoglycosides (x=1), in which a sugar unit is attached to the fatty alcohol by a glycoside bond, and oligomeric glycosides having a degree of oligomerization x of 2 to 10 are suitable. Mixtures of monoglycosides and oligoglycosides are normally present. Particularly suitable are alkyl glycosides (B) corresponding to the formula $R^1$-$(G)_x$, in which $R^1$ is a $C_{8-18}$ alkyl group and $(G)_x$ is a glucoside or oligoglucoside having a degree of oligomerization x of 1 to 4. In a particularly preferred embodiment, $R^1$ is a $C_{12-16}$ group and $-(G)_x$ is the residue of a mixture of glucosides and oligoglucosides having an average degree of oligomerization $x=1-2$.

In addition to the compulsory components (A) and (B), which preferably are present in a total amount of at least 5% by weight of the total preparation, the aqueous detergent preparations according to the invention may also contain other surfactants and additives, although no more than 20% by weight other surface-active agents should be present.

If the total content of components (A) and (B) is below 20% by weight and the content of component (B) is below 8% by weight, the viscosity of detergent preparations according to the invention may still be unsatisfactory. However, it is of particular advantage of the preparations according to the invention that, in cases such as these, viscosity may readily be increased by addition of water soluble inorganic electrolyte salts or even by addition of an amphoteric or zwitterionic surfactant or by addition of both products.

In one preferred embodiment, therefore, the detergent preparations according to the invention additionally contain (C) 1 to 8% by weight of an amphoteric or zwitterionic surfactant and/or
(D) 0.1 to 5% by weight of a water-soluble inorganic electrolyte salt.

Amphoteric surfactants (C) are characterized by a lipophilic alkyl or acyl group and a carboxyl group. Examples of suitable amphoteric surfactants are, for example, N-($C_{12-18}$)-alkylaminoacetic acid, N-($C_{12-18}$)-acylaminopropyl aminopropionic acid. Zwitterionic surfactants are distinguished by a lipophilic alkyl or acyl containing 8 to 18 carbon atoms, a quaternary ammonium group and a carboxyl group. Examples of suitable zwitterionic surfactants (C) are N-($C_{12-18}$)-alkyl-N,N-dimethyl glycinate, N-($C_{12-18}$)-acylaminopropyl-N,N-dimethyl glycinate, N-($C_{12-18}$)-acylaminoethyl-N,N-dimethyl glycinate, N-($C_{12-18}$)-acylaminopropyl-N-methyl-N-hydroxyethyl glycinate, 2-($C_{12-18}$)-alkyl-1-carboxymethyl-3-hydroxyethyl imidazoline.

Suitable inorganic electrolyte salts (D) are any water soluble alkali metal, ammonium and alkaline earth metal salts, for example the fluorides, chlorides, bromides, sulfates, phosphates, nitrates and hydrogen carbonates providing they are soluble in water in a quantity of at least 1% by weight at 20° C. The chlorides or sulfates of an alkali metal or magnesium are preferably used. Sodium chloride and magnesium chloride are particularly effective.

The rheological properties of the detergent compositions according to the invention are particularly good above all when the sum of components (A)+(B)+(C)+(D) is at least 8% by weight of the composition as a whole.

In addition, the preparations according to the invention may contain other components which make them particularly suitable for the particular application envisaged. For example, other nonionic or anionic surfactants may be present, the quantity in which they are present preferably being gauged so that, in addition to (A) and (B), no more than 20% by weight of other surface-active agents are present.

Finally, fragrances, dyes, opacifiers and pearlescers, antimicrobial agents, preservatives, antioxidants, skin-cosmetic agents, vegetable extracts, protein hydrolyzates, buffers, complexing agents, water-soluble polymers, layer silicates and other known auxiliaries and additives of the type typically used in shampoos, bath additives, shower bath preparations, liquid soaps, skin cleaning liquids or pastes, liquid hair rinses and in liquid fine-duty detergents and dishwashing detergents and liquid domestic cleaners may also be present in small quantities.

The following Examples are intended to illustrate the invention.

EXAMPLES

The following test substances were used:

PFC = Collagen hydrolyzate/coconut oil ($C_{12-18}$) condensate, Na salt (the commercial product Lamepon® S was used in the form of a 30% aqueous solution)

APG = Alkyl ($C_{12-14}$) glucoside (the alkyl group corresponds to the C chain distribution of a $C_{12-14}$ coconut oil fatty alcohol fraction; the average degree of oligomerization x is 1.4) in the form of a 50% aqueous solution.

Test formulations 1 to 10 of Tables I and II were prepared by mixing the components at 20° C.

RESULTS

The viscosity of the formulations was measured at 20° C. using a Haake type RV3 rotational viscosimeter. The results are set out in Table I.

The foaming power of the formulations was determined in a so-called standardized bath tub test. To this end, 0.01% solution of the test formulation was prepared in a bath tub (15 g to 150 l of water at 20° C.) and was foamed by inflowing water. The foam formed under defined conditions (time, water pressure) was volumetrically measured. The results are set out in Table II.

TABLE 1

| Composition* | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| PFC | 15 | 15 | 7.5 | 9 | 10 | 10 | 12 | 12 | 8 | 8 | 4 | 4 | 5 | 5 | 3 | 3 |
| APG | — | — | 12.5 | 10 | 8.5 | 8.5 | 5 | 5 | — | — | 4 | 4 | 3 | 3 | 5 | 5 |
| NaCl | — | 1-3 | — | — | — | 0.5 | — | 2 | — | 1-5 | — | 1.5 | — | 2 | — | 1.2 |
| $H_2O$ | 85 | 82-84 | 80 | 81 | 81 | 81 | 83 | 81 | 92 | 87-91 | 92 | 90.5 | 92 | 90 | 92 | 90.8 |
| Viscosity (20° C., Pa·sec) | Under 0.1 | Under 0.1 | 4.95 | 14.3 | 4.35 | 13.35 | Under 0.1 | 2.55 | Under 0.1 | Under 0.1 | Under 0.1 | 1.4 | Under 0.1 | 2.7 | Under 0.1 | 8.2 |

*in % by weight active substance

TABLE 2

| Composition* | 17 | 18 | 19 | 3 | 4 | 20 | 9 | 11 | 13 | 15 |
|---|---|---|---|---|---|---|---|---|---|---|
| PFC | 20 | — | 6 | 7.5 | 9 | — | 8 | 4 | 5 | 3 |
| APG | — | 25 | 15 | 12.5 | 10 | 8 | — | 4 | 3 | 5 |
| $H_2O$ | 80 | 75 | 79 | 80 | 81 | 92 | 92 | 92 | 92 | 92 |
| Foam volume [l] at 20° C. | 2 | 13 | 18 | 21 | 23 | 10 | 1 | 19 | 16 | 20 |

*in % by weight active substance

The invention claimed is:

1. A water-based detergent preparation, comprising:
   (A) from 1 to 20% by weight of a condensation product of fatty acids containing 12 to 22 carbon atoms with a component selected from the group consisting of water-soluble oligo- and poly-peptides, water soluble salts thereof, and mixtures thereof; and
   (B) from 1 to 20% by weight of an alkyl glycoside corresponding to the formula $R^1$-$(G)_x$, in which $R^1$ is an alkyl group containing 8 to 22 carbon atoms and $(G)_x$ is a glycoside or oligoglycoside unit having a degree of oligomerization x of 1 to 10.

2. A water-based detergent preparation as claimed in claim 1, wherein the sum of the condensation product (A) and the alkyl glycoside (B) is at least 5% by weight and no more than 20% by weight of other surface-active agents are present.

3. A water-based detergent preparation as claimed in claim 2, wherein component (A) is selected from the group consisting of condensation products of $C_{12-18}$ fatty acids with water soluble protein hydrolyzates.

4. A water-based detergent preparation as claimed in claim 3, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

5. A water-based detergent preparation as claimed in claim 2, additionally comprising at least one of:
   (C) from 1 to 8% by weight of an amphoteric or zwitterionic surfactant; and
   (D) from 0.1 to 5% by weight of a water-soluble inorganic electrolyte salt.

6. A water-based detergent preparation as claimed in claim 5, wherein component (A) is selected from the group consisting of condensation products of $C_{12-18}$ fatty acids with water soluble protein hydrolyzates.

7. A water-based detergent preparation as claimed in claim 6, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

8. A water-based detergent preparation as claimed in claim 5, wherein the sum of components (A)+(B)+(C)+(D) is at least 8% by weight.

9. A water-based detergent preparation as claimed in claim 8, wherein component (A) is selected from the group consisting of condensation products of $C_{12-18}$ fatty acids with water soluble protein hydrolyzates.

10. A water-based detergent preparation as claimed in claim 9, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

11. A water-based detergent preparation as claimed in claim 1, additionally comprising at least one of:
   (C) from 1 to 8% by weight of an amphoteric or zwitterionic surfactant; and
   (D) from 0.1 to 5% by weight of a water-soluble inorganic electrolyte salt.

12. A water-based detergent preparation as claimed in claim 11, wherein component (A) is selected from the group consisting of condensation products of $C_{12-18}$ fatty acids with water soluble protein hydrolyzates.

13. A water-based detergent preparation as claimed in claim 12, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

14. A water-based detergent preparation as claimed in claim 11, wherein the sum of components (A)+(B)+(C)+(D) is at least 8% by weight.

15. A water-based detergent preparation as claimed in claim 14, wherein component (A) is selected from the group consisting of condensation products of $C_{12-18}$ fatty acids with water soluble protein hydrolyzates.

16. A water-based detergent preparation as claimed in claim 15, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

17. A water-based detergent preparation as claimed in claim 14, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

18. A water-based detergent preparation as claimed in claim 11, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

19. A water-based detergent preparation as claimed in claim 1, wherein component (A) is selected from the group consisting of condensation products of $C_{12-18}$ fatty acids with water soluble protein hydrolyzates.

20. A water-based detergent preparation as claimed in claim 19, wherein component (B) is selected from the group consisting of alkyl glycosides corresponding to the formula $R^1\text{-}(G)_x$, in which $R^1$ is a $C_{12-16}$ alkyl group and $(G)_x$ is the residue of a mixture of glucosides and oligoglucosides having an average degree of oligomerization from 1 to 2.

* * * * *